United States Patent
Ra et al.

(10) Patent No.: US 11,932,874 B2
(45) Date of Patent: Mar. 19, 2024

(54) METHOD FOR CULTURING MESENCHYMAL STEM CELLS USING GAMMA-IRRADIATED SERUM

(71) Applicants: R Bio CO., Ltd., Seoul (KR); NATURECELL CO., LTD., Seoul (KR); Jung-Chan Ra, Chungcheongbuk-do (KR)

(72) Inventors: Jeong Chan Ra, Chungcheongbuk-do (KR); Sung Keun Kang, Seoul (KR); Eun-Young Kim, Seoul (KR)

(73) Assignees: R BIO CO., LTD., Seoul (KR); NATURECELL CO., LTD., Seoul (KR); Jung-Chan Ra, Chungcheongbuk-Do (KR)

( * ) Notice: Subject to any disclaimer, the term of this patent is extended or adjusted under 35 U.S.C. 154(b) by 307 days.

(21) Appl. No.: 16/422,525

(22) Filed: May 24, 2019

(65) Prior Publication Data
US 2019/0359942 A1  Nov. 28, 2019

(30) Foreign Application Priority Data

May 25, 2018  (KR) ......................... 10-2018-0059594
May 23, 2019  (KR) ......................... 10-2019-0060757

(51) Int. Cl.
*C12N 5/077* (2010.01)

(52) U.S. Cl.
CPC ........ *C12N 5/0653* (2013.01); *C12N 2500/38* (2013.01)

(58) Field of Classification Search
None
See application file for complete search history.

(56) References Cited

U.S. PATENT DOCUMENTS

2013/0134849 A1* 5/2013 Menzel ................ A47B 95/008
312/265.5

FOREIGN PATENT DOCUMENTS

| JP | 2007525990 A | 9/2007 |
| JP | 2012512654 A | 6/2012 |
| JP | 2015526067 A | 9/2015 |
| JP | 2017532973 A | 11/2017 |
| KR | 20160050412 A | 5/2016 |

OTHER PUBLICATIONS

Larijani et al., Acta Medica Iranica, vol. 53, No. 9 (2015) (Year: 2015).*
Lin et al., Stem Cells and Development 14: 92-102 (2005) (Year: 2005).*
Brown et al., PharmacyTimes.com, Fighting Free Radicals: Do You need Antioxidants?, 7 pages, retrieved from the internet Nov. 8, 2021: https://www.pharmacytimes.com/view/fighting-free-radicals-do-you-need-antioxidants (Year: 2021).*
Fujisawa et al, Stem Cell Research & Therapy (2018) 9:93, 12 pages (Year: 2018).*
Potdar et al., Human Cell 2010; 23: 152-155 (Year: 2010).*
Zhang Organogenesis, 12:143-151, 2016 (Year: 2016).*
Abecasis, M., et al., "A potential role for mesenchymal stem cells in allogeneic bone marrow transplantation for familial haemophagocytic lymphohistiocytosis", "Bone Marrow Transplantation", 2010, p. S327, Abstract No. P1033, vol. 45, No. 2.
Mugishima, H., et al., "Development of novel cell therapies using stem cells in umbilical cord blood and cord tissue", "Bulletin of Institute of Medical Science, Hihon University School of Medicine", 2013, pp. 1-7, vol. 1.
Mugishima, H., et al., "Development of novel cell therapies using stem cells in umbilical cord blood and cord tissue", "Bulletin of Institute of Medical Science, Nihon University School of Medicine", 2013, pp. 1-7, vol. 1, Eng Abst.
Akutsa, H., et al., "Xenogeneic-free Defined Conditions for Derivation and Expansion of Human Embryonic Stem Cells with Mesenchymal Stem Cells", "Regenerative Therapy", 2015, pp. 18-29, vol. 1.
Bienvenu, P., et al., "Antioxidant Effects in Radioprotection", "Advances in Experimental Medicine and Biology", 1990, pp. 291-300; Abstract, vol. 264.
Cho, Y., "Change of Characteristics of Bovine Serum Albumin, beta-Lactoglobulin and Food Proteins by γ-Irradtion", "Chungnam National University Dissertation", 1999, pp. 1-125.
Davies, K., "Protein Damage and Degradation by Oxygen Radicals", "The Journal of Biological Chemistry", 1987, pp. 9895-9901, vol. 262, No. 20.
El-Nahas, S., et al., "Radioprotective Effect of Vitamins C and E", "Mutation Research", 1993, pp. 143-147, vol. 301.
Garrison, W.M., "Reaction Mechanisms in the Radiolysis of Peptides, Polypeptides, and Proteins", "Chem. Rev.", 1987, pp. 381-398, vol. 87.
Kim, J., et al., "Sterilization Characteristics of Ionizing Irradiation and Its Industrial Application", "Journal of Korean Musculoskeletal Tissue Transplantation Society", Dec. 2013, pp. 49-57, vol. 13, No. 2.

(Continued)

*Primary Examiner* — Evelyn Y Pyla
(74) *Attorney, Agent, or Firm* — HULTQUIST, PLLC; Steven J. Hultquist

(57) ABSTRACT

The present invention relates to a method of culturing mesenchymal stem cells using gamma-irradiated serum, and more particularly to a method for culturing mesenchymal stem cells, which can improve the adhesion and proliferation rate of stem cells using a medium containing gamma-irradiated serum and an antioxidant. The method for culturing mesenchymal stem cells according to the present invention can restore the adhesion and proliferation rate of stem cells when culturing the stem cells using gamma-irradiated FBS, which is safe from contamination sources but reduces the efficiency of adhesion and proliferation of the cells. Thus, the inventive method is useful for the production of stem cells for cell therapy.

5 Claims, 13 Drawing Sheets
(13 of 13 Drawing Sheet(s) Filed in Color)

(56) References Cited

OTHER PUBLICATIONS

Krumhar, K., et al., "Effect of Antioxidant and Conditions on Solubiliy of Irradiated Food Proteins in Aqueous Solutions", "Journal of Food Science", 1990, pp. 1127-1132, vol. 55, No. 4.

Mannello, F., et al., "Concise Review: No Breakthroughs for Human Mesenchymal and Embryonic Stem Cell Culture: Conditioned Medium, Feeder Layer, or Feeder-Free; Medium with Fetal Calf Serum, Human Serum, or Enriched Plasma; Serum-Free, Serum Replacement NonConditioned Medium . . . ", "Stem Cells", 2007, pp. 1603-1609, vol. 25, No. 7.

Maurer, H.R., "Introductory Remarks", "Cytotechnology", 1991, p. 1, vol. 5.

Niki, E., et al., "Inhibition of Oxidation of Methyl Linoleate in Solution by Vitamin E and Vitamin C", "The Journal of Biological Chemistry", 1984, pp. 4177-4182, vol. 259, No. 7.

Niki, E., "Interaction of Ascorbate and alpha-Tocopherol", "Ann. N.Y. Acad. Sci.", 1987, pp. 186-199, vol. 498.

O'Connor, M., et al., "A Radioprotective Effect of Vitamin C Observed in Chinese Hamster Ovary Cells", "British Journal of Radiology", Aug. 1977/, pp. 587-591, vol. 50.

Singh, A., et al., "Radioprotection by Ascorbic Acid, Desferal, and Mercaptoethylamine", "Methods in Enzymology", 1990, pp. 686-696, vol. 186.

Stein, A., "Decreasing Variability in Your Cell Culture", "Biotechniques", 2007, pp. 228-229, vol. 43, No. 2.

Sterodimas, A., et al., "Tissue Engineering with Adipose-Derived Stem Cells (ADSCs): Current and Future Applications", "Journal of Plastic, Reconstructive and Aesthetic Surgery", 2010, pp. 1886-1892, vol. 63.

Wong, R., "Mesenchymal Stem Cells: Angels or Demons?", "Journal of Biomedicine and Biotechnology", 2011, pp. 1-8, vol. 2011.

Yook, H., et al., "Changes of Proteolytic Enzyme Property by Gamma Irradiation", "J. Korean Soc. Food Sci. Nutr.", 1997, pp. 1116-1121, vol. 26, No. 6.

\* cited by examiner

[Fig. 1]
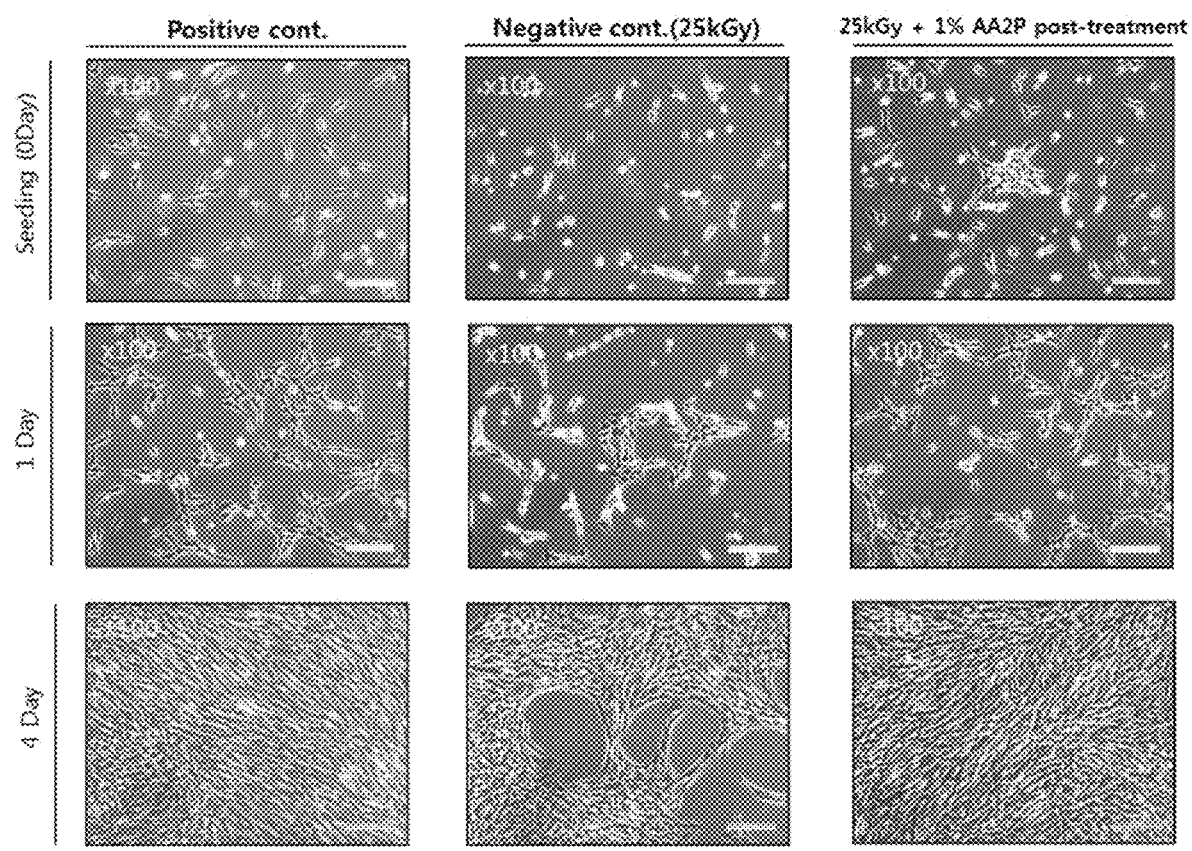

[Fig. 2]
A.
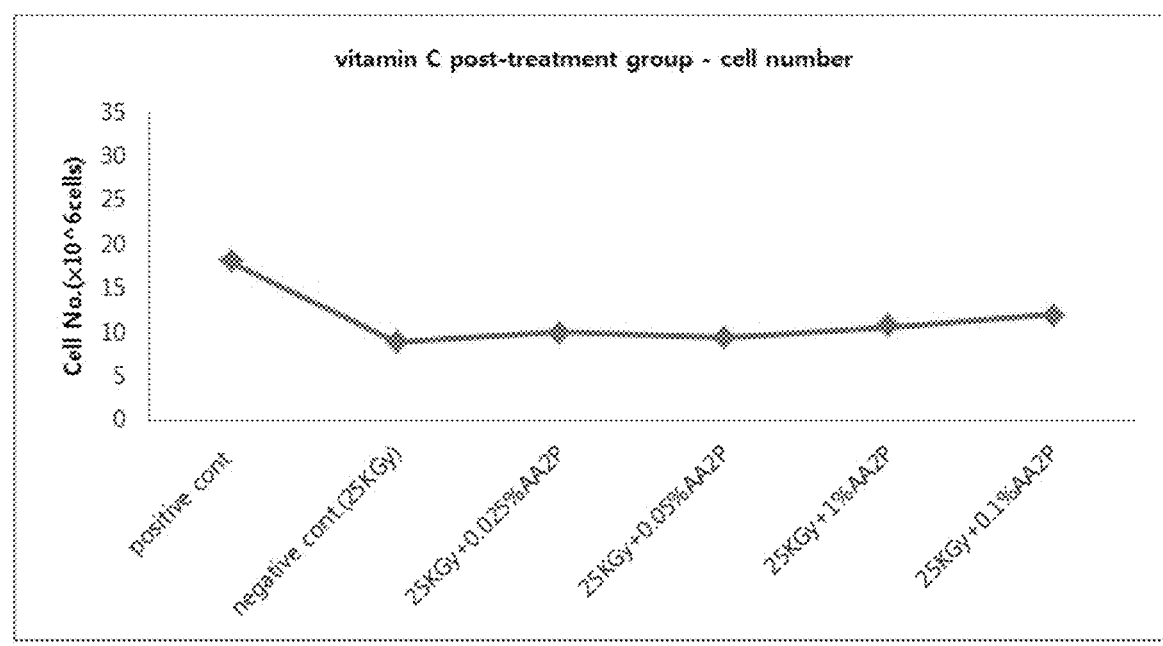

[Fig. 2] (continued)
B.
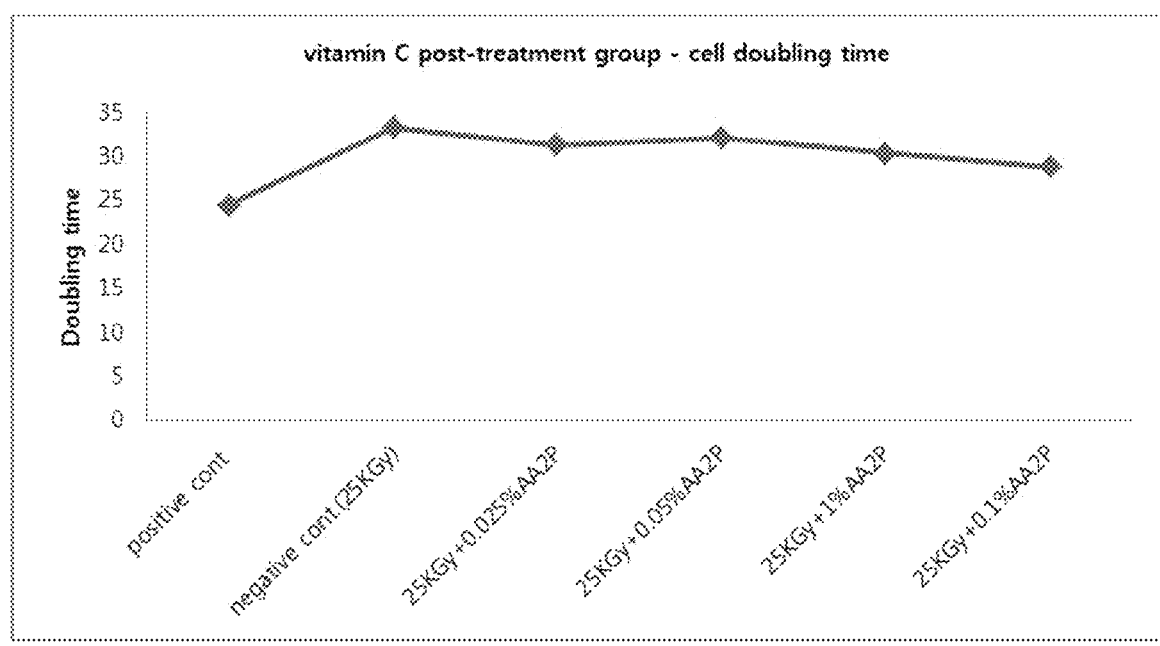

[Fig. 3]
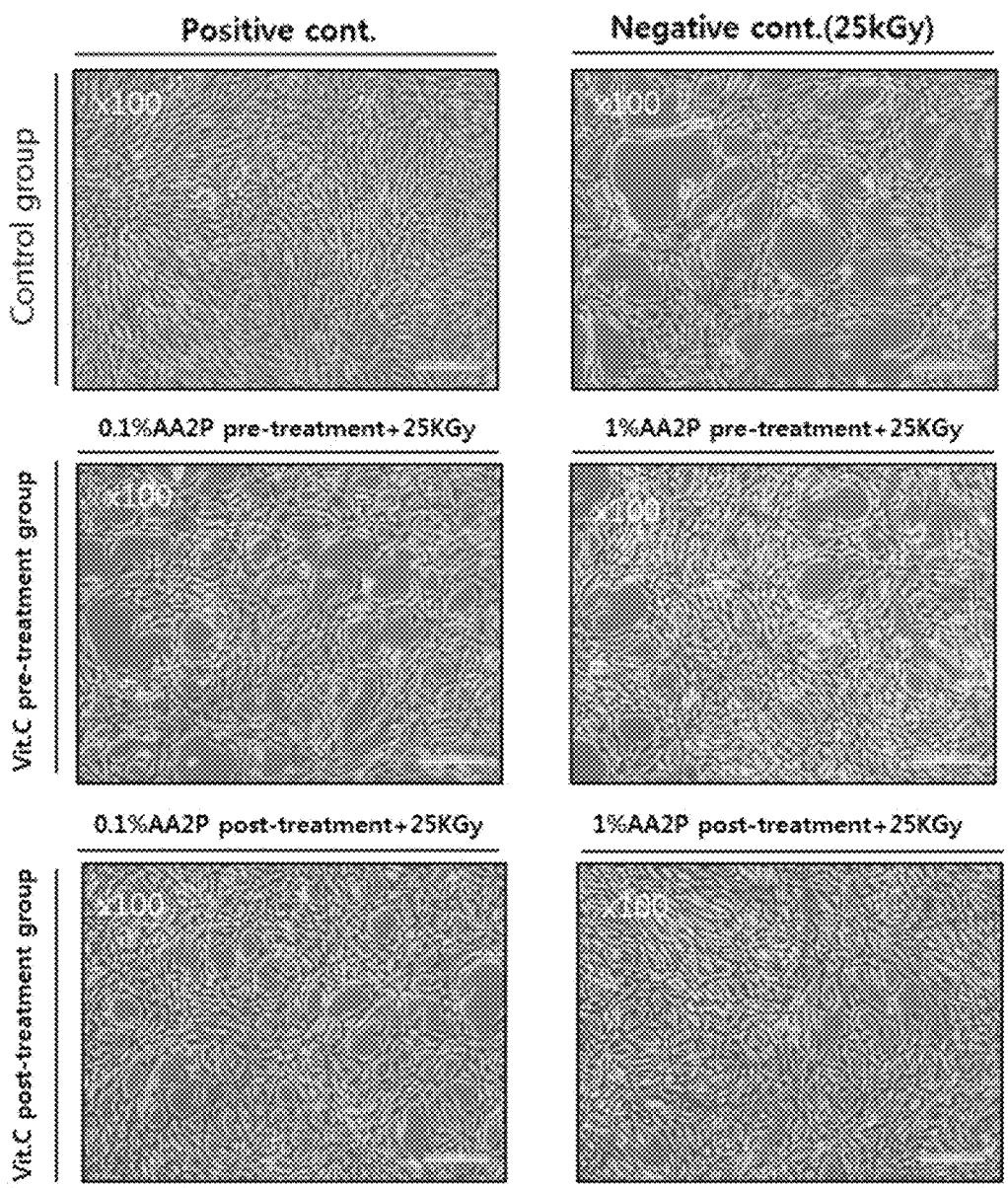

[Fig. 4]
A.
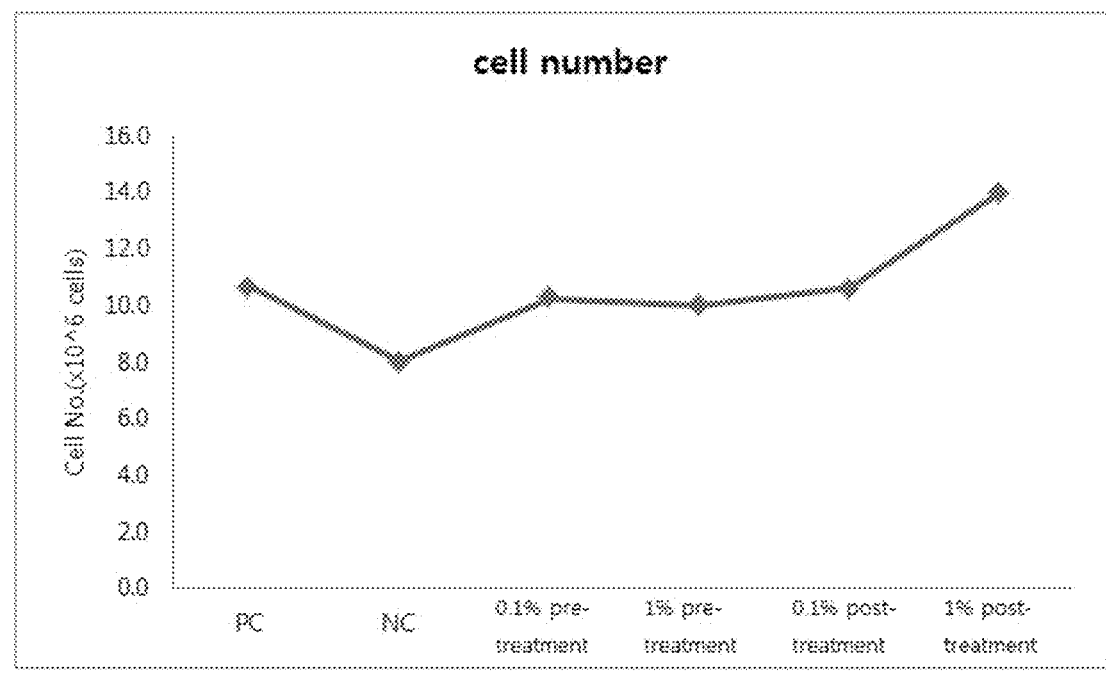
B.
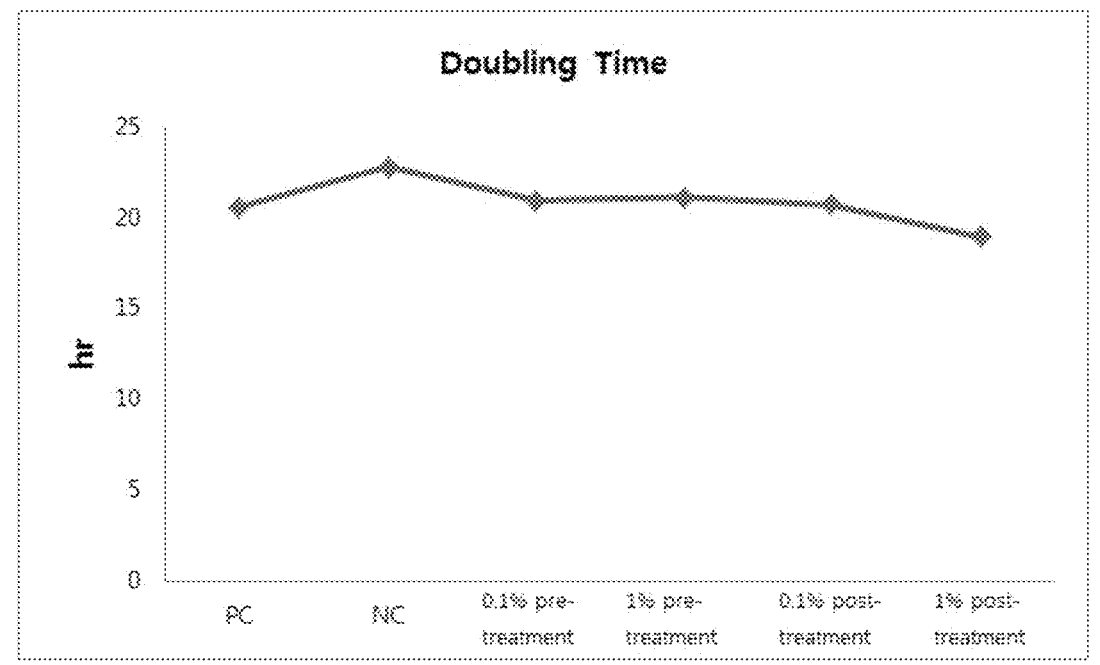

【Fig. 5】
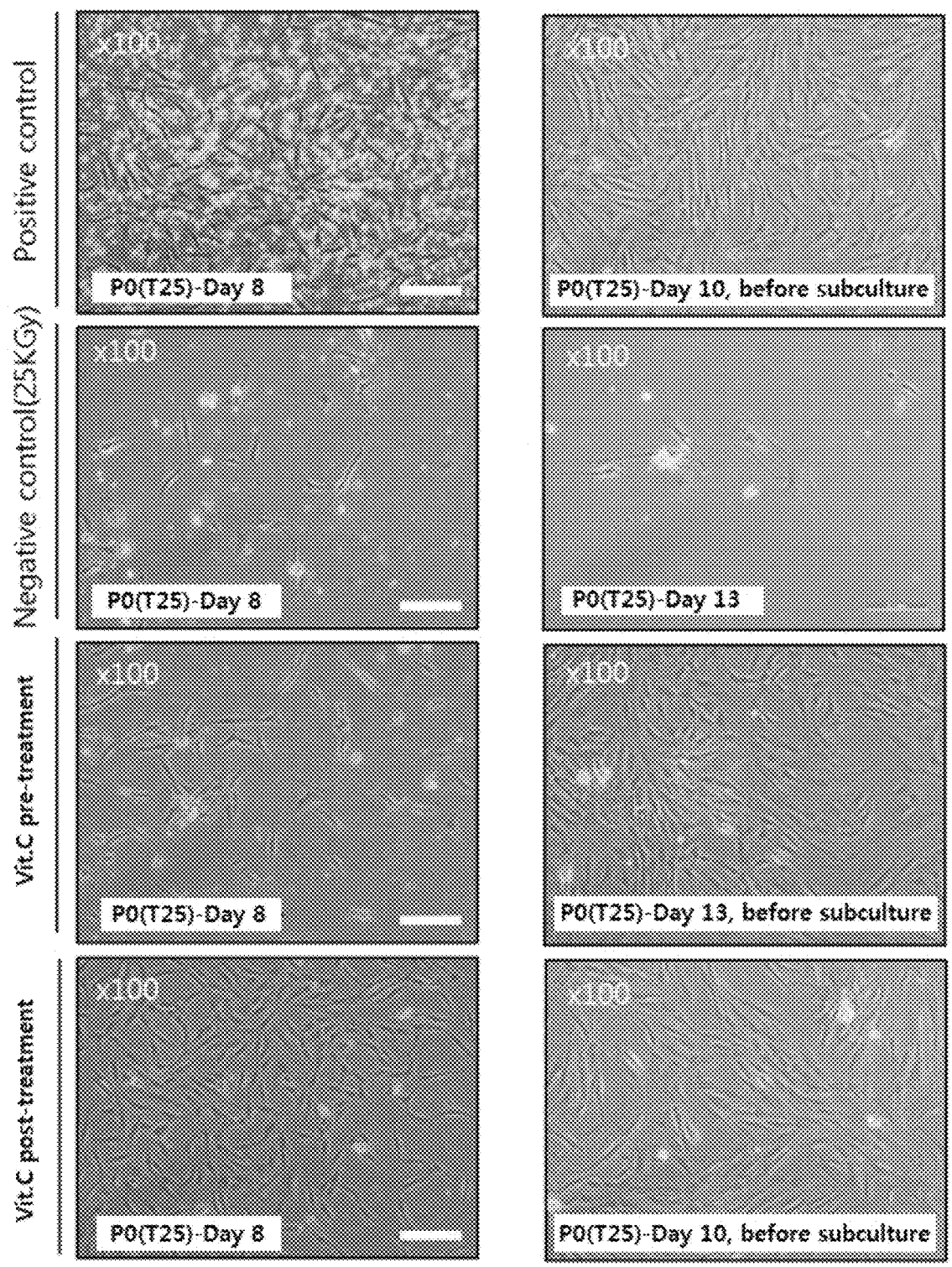

[Fig. 6]
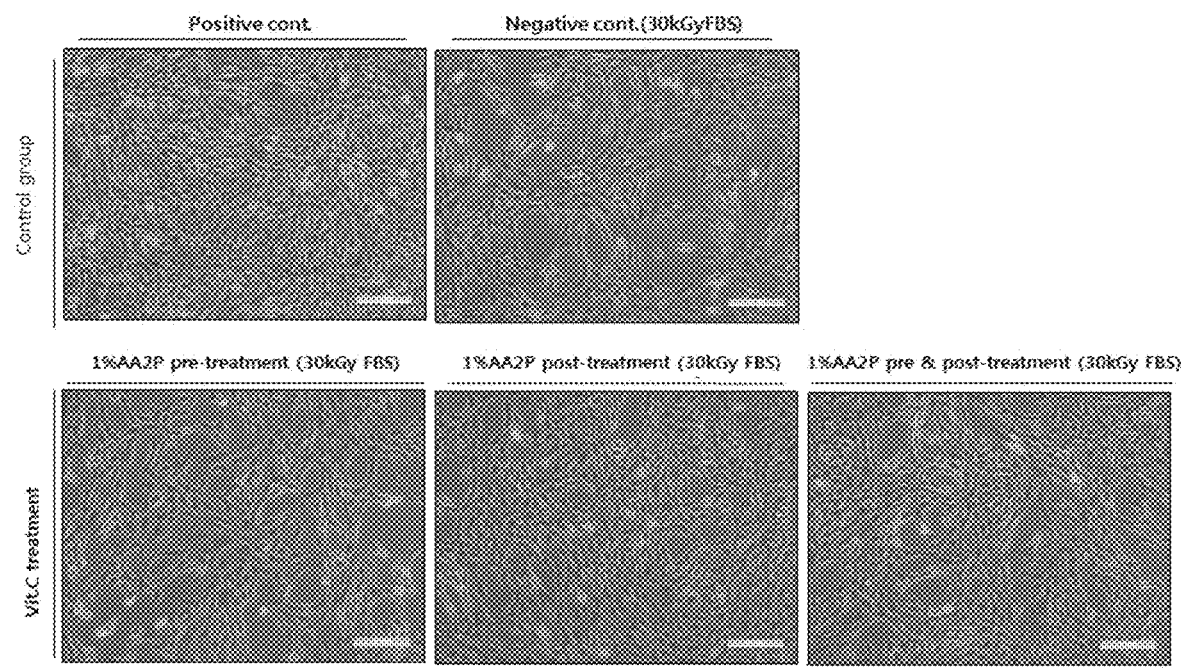
[Fig. 7]
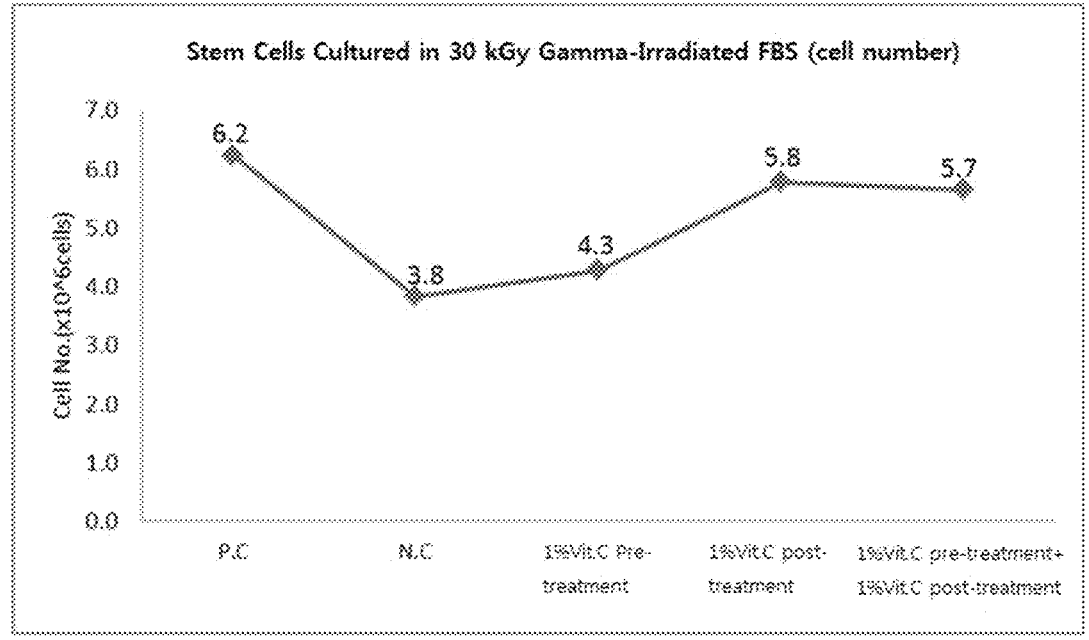

[Fig. 8]
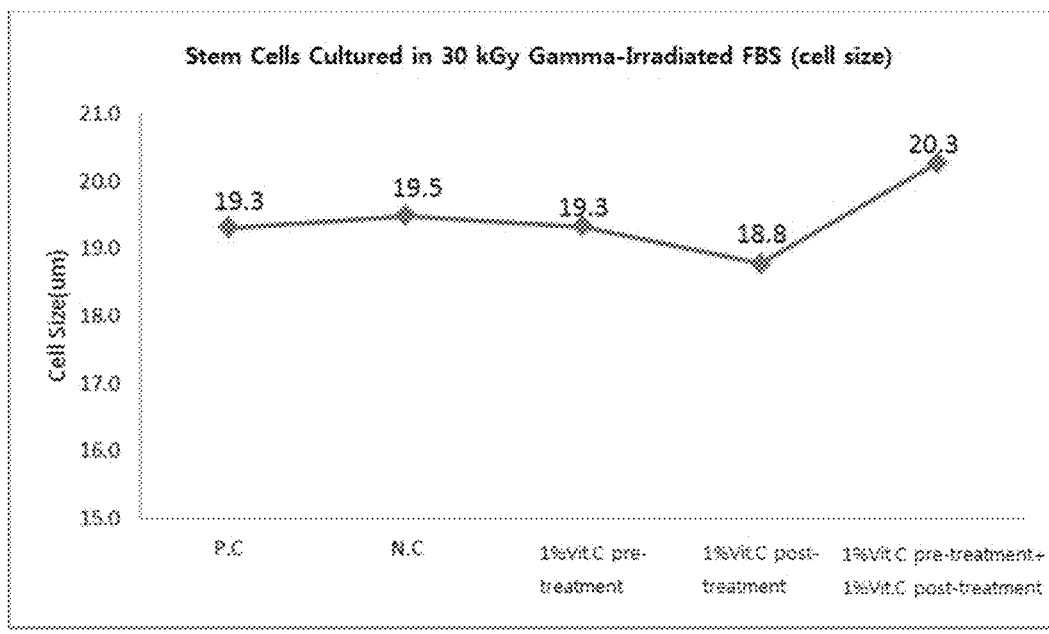
[Fig. 9]
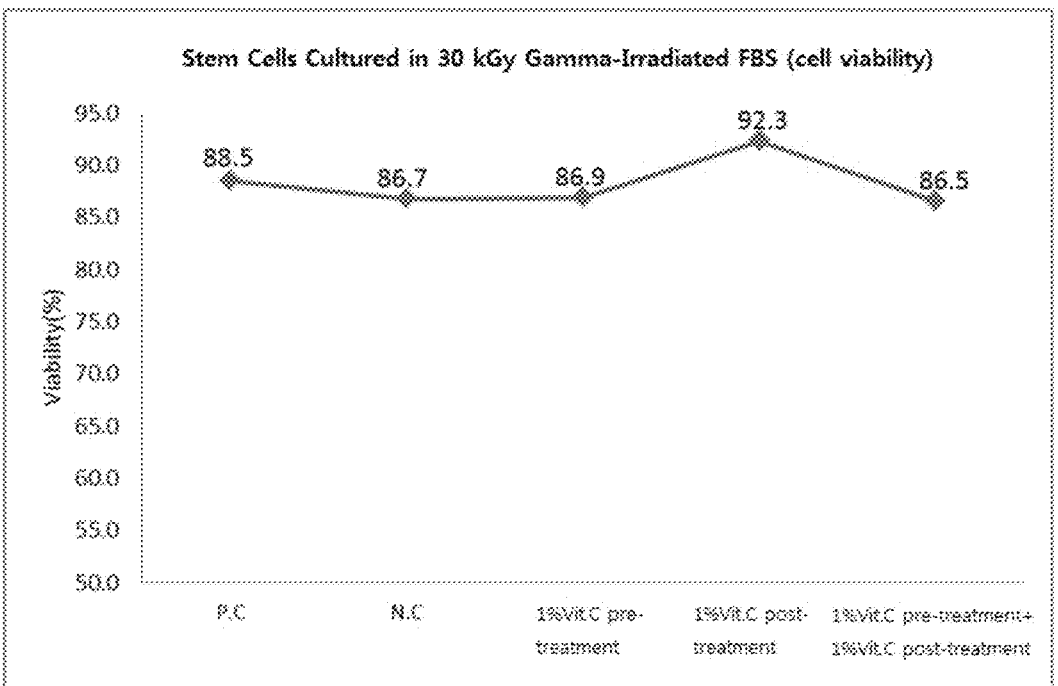

[Fig. 10]
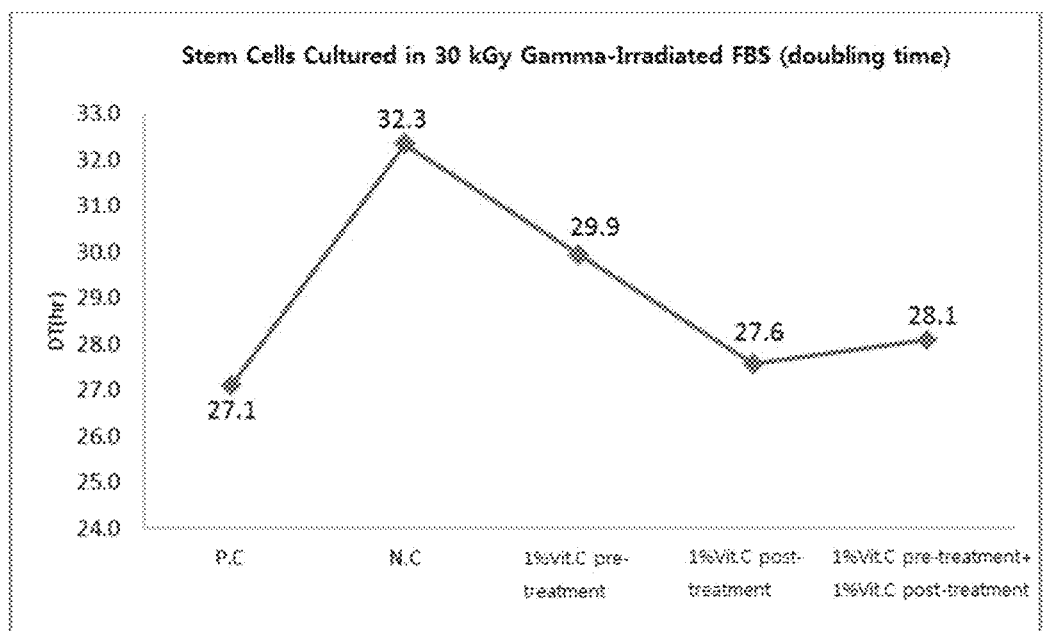
[Fig. 11A]
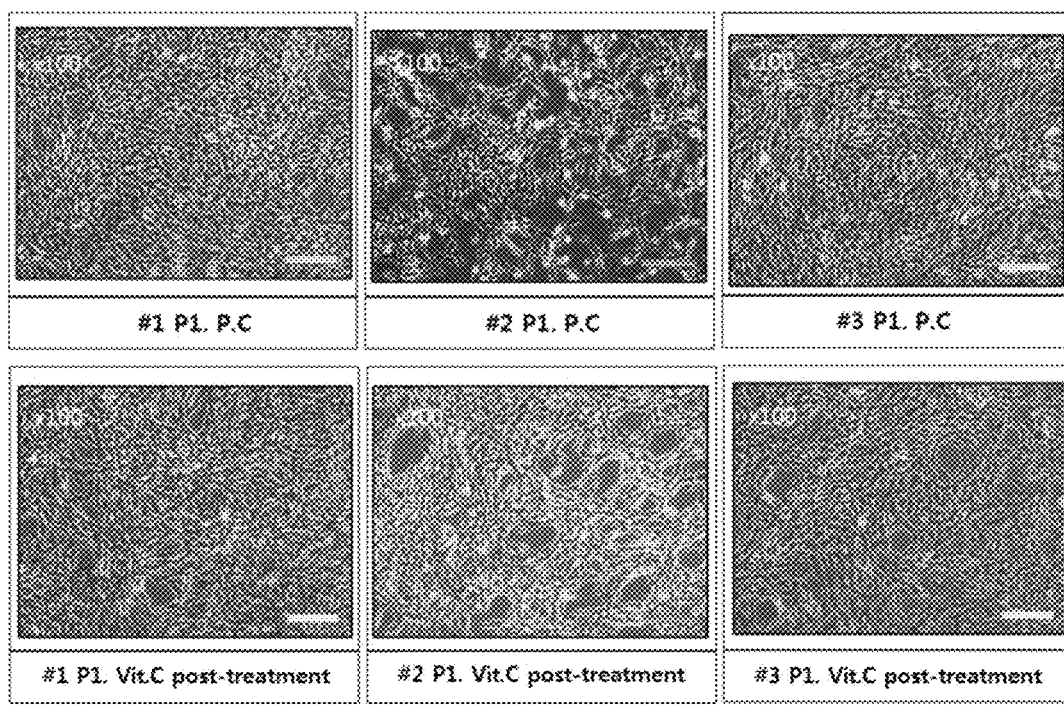

[Fig. 11B]
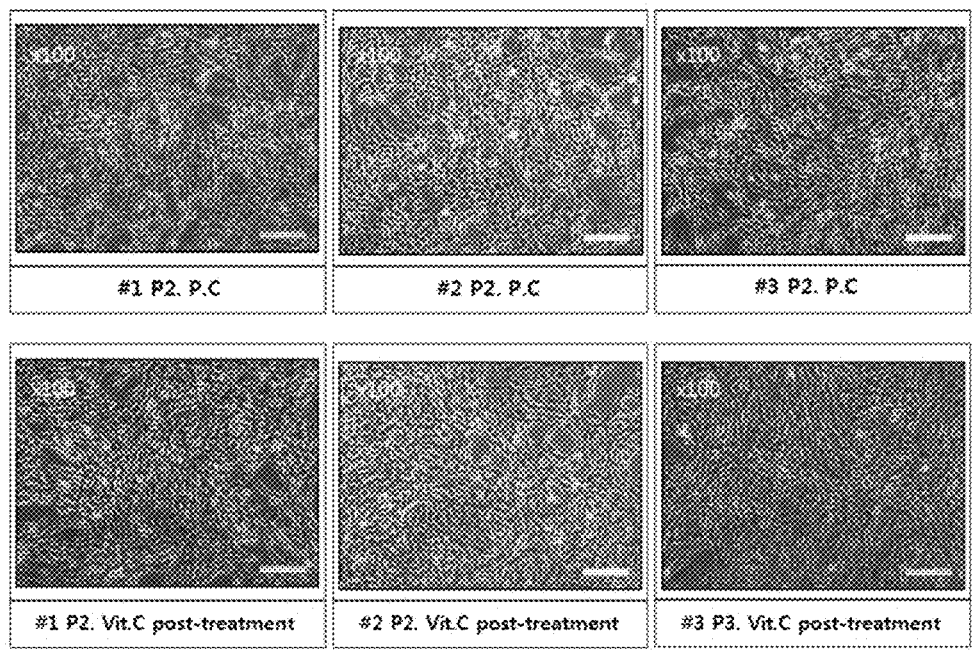
[Fig. 11C]
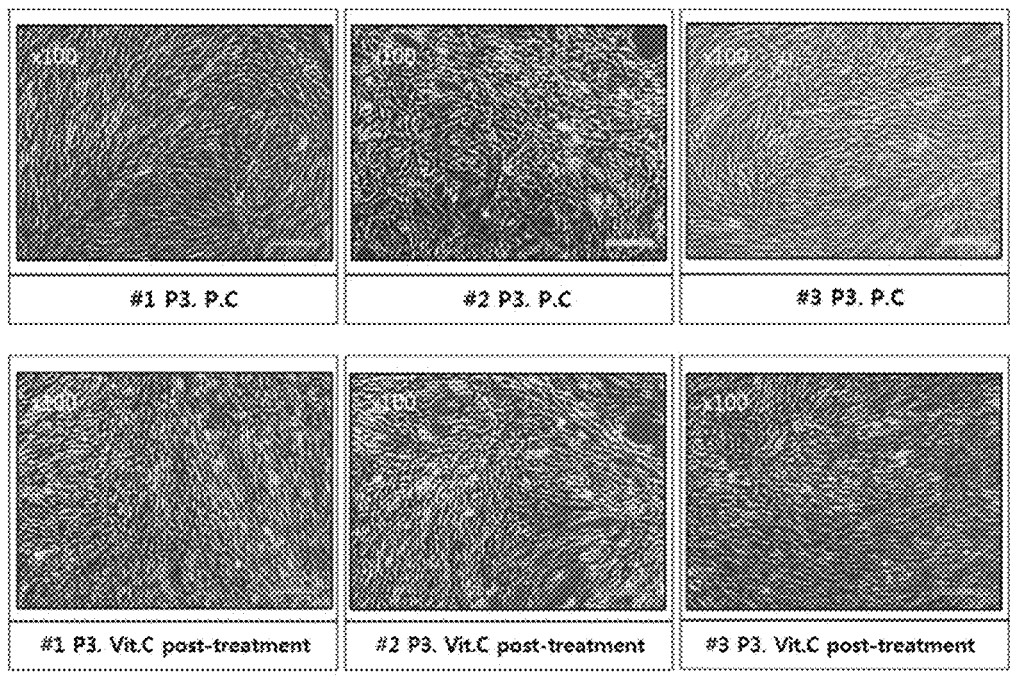

[Fig. 12]
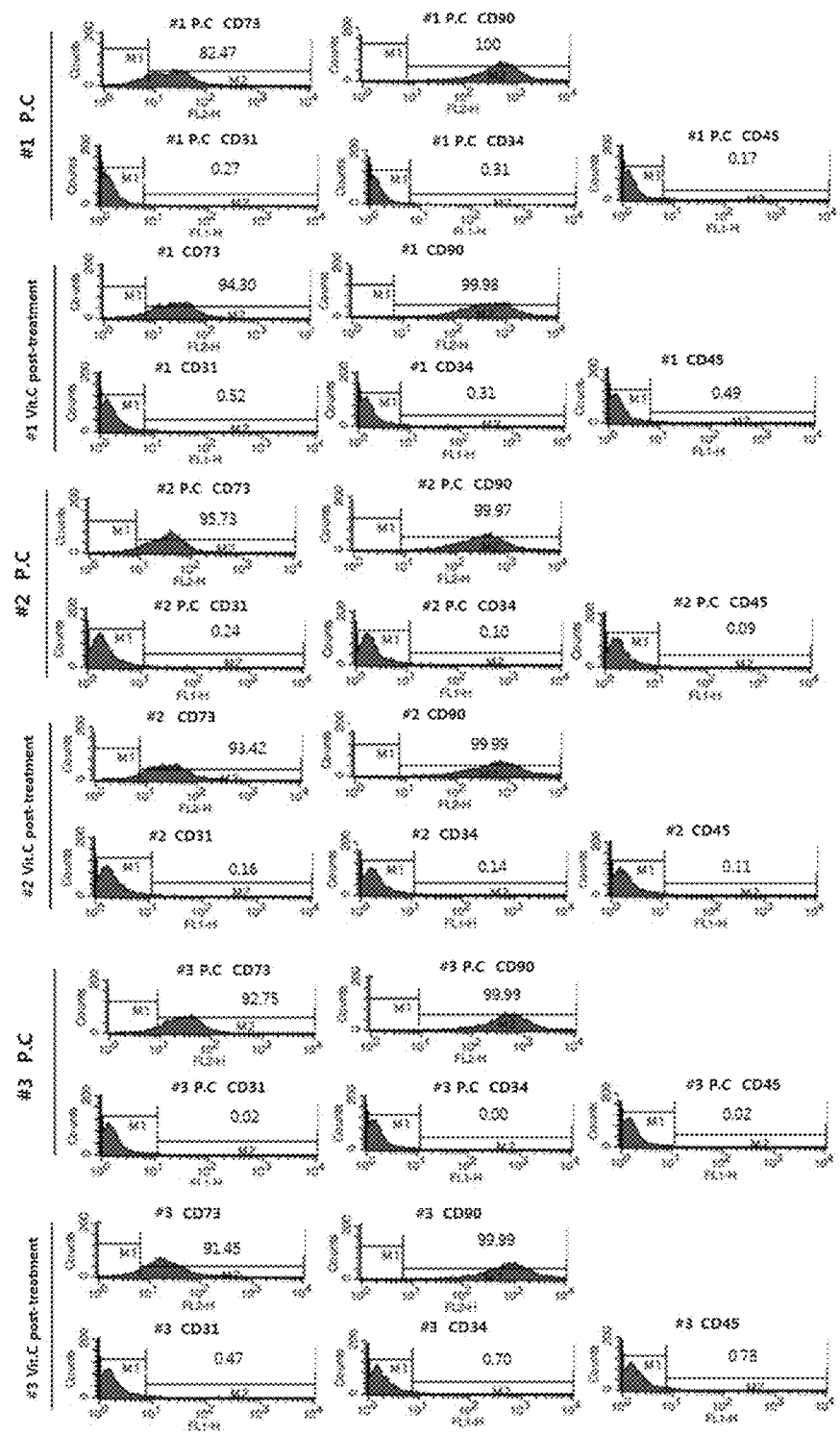

[Fig. 13]
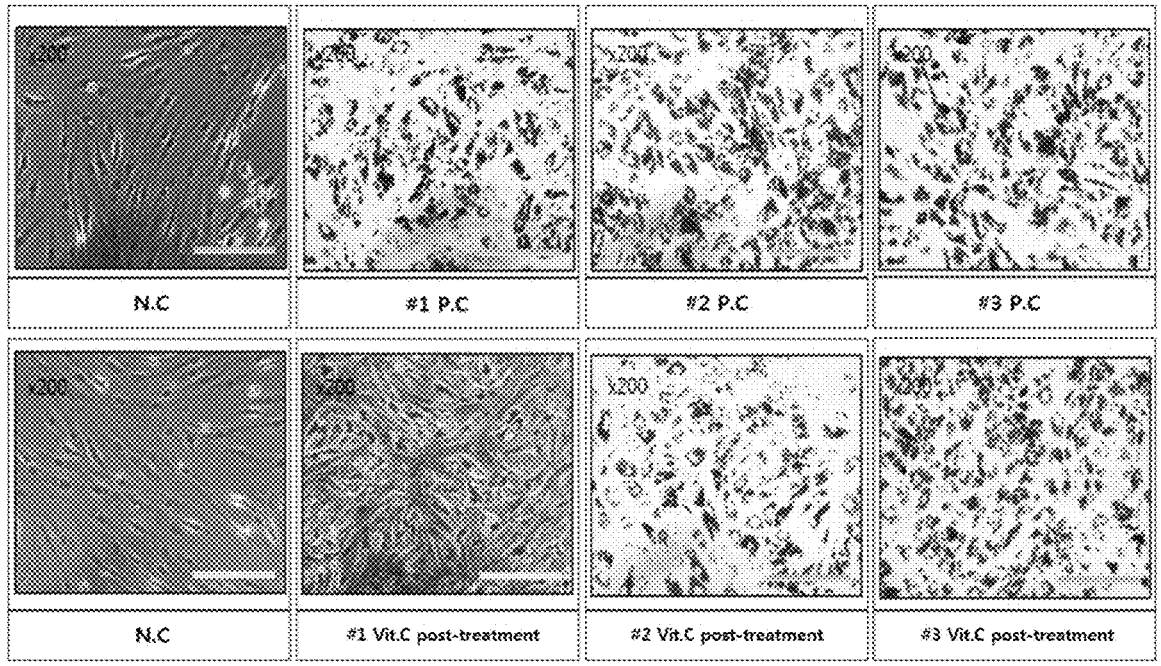
[Fig. 14]
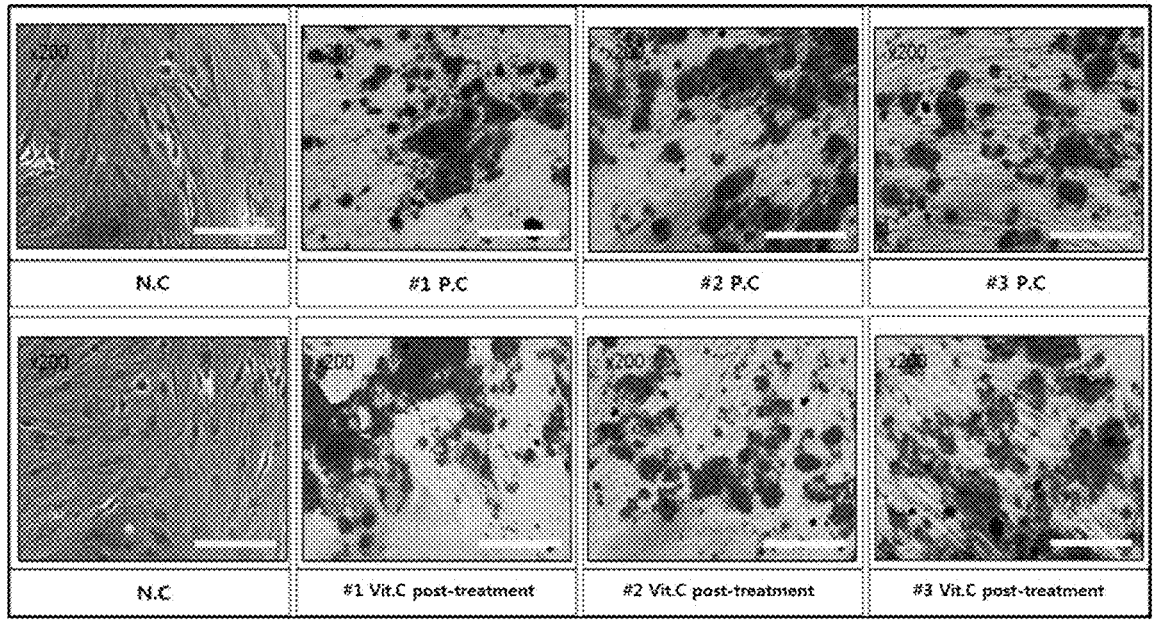

[Fig. 15]
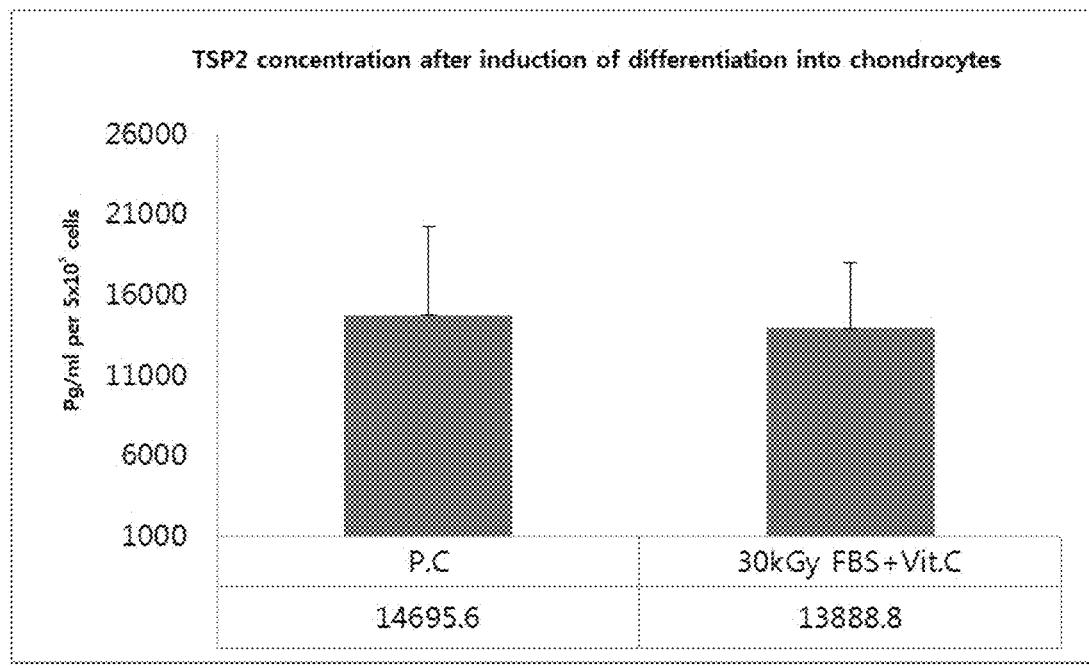

METHOD FOR CULTURING MESENCHYMAL STEM CELLS USING GAMMA-IRRADIATED SERUM

CROSS-REFERENCE TO RELATED APPLICATIONS

The priority under 35 USC § 119 of Korean Patent Application 10-2018-0059594 filed May 25, 2018 and Korean Patent Application 10-2019-0060757 filed May 23, 2019 is hereby claimed. The disclosures of Korean Patent Application 10-2018-0059594 and Korean Patent Application 10-2019-0060757 are hereby incorporated herein by reference, in their entireties, for all purposes.

TECHNICAL FIELD

The present invention relates to a method of culturing mesenchymal stem cells using gamma-irradiated serum, and more particularly to a method for culturing mesenchymal stem cells, which can improve the adhesion and proliferation rate of stem cells using a medium containing gamma-irradiated serum and an antioxidant.

BACKGROUND ART

Stem cells refer to cells having not only self-replicating ability but also the ability to differentiate into at least two types of cells, and can be divided into totipotent stem cells, pluripotent stem cells, and multipotent stem cells.

Stem cells refer to cells having not only self-replicating ability but also the ability to differentiate into at least two types of cells, and can be divided into totipotent stem cells, pluripotent stem cells, and multipotent stem cells. Totipotent stem cells are cells having totipotent properties capable of developing into one perfect individual, and these properties are possessed by cells up to the 8-cell stage after the fertilization of an oocyte and a sperm. When these cells are isolated and transplanted into the uterus, they can develop into one perfect individual. Pluripotent stem cells, which are cells capable of developing into various cells and tissues derived from the ectodermal, mesodermal and endodermal layers, are derived from an inner cell mass located inside of blastocysts generated 4-5 days after fertilization. These cells are called "embryonic stem cells" and can differentiate into various other tissue cells but not form new living organisms. Multipotent stem cells, which are stem cells capable of differentiating into only cells specific to tissues and organs containing these cells, are involved not only in the growth and development of various tissues and organs in the fetal, neonatal and adult periods but also in the maintenance of homeostasis of adult tissue and the function of inducing regeneration upon tissue damage. Tissue-specific multipotent cells are collectively called "Mesenchymal stem cells".

Mesenchymal stem cells (Rebecca S. Y. Wong, et al., *J Biomed Biotechnol* 24:2011, 2011) have been used in cell-based therapies in a variety of disease conditions, such as heart disease, osteogenesis imperfecta and spinal cord injury, and the results thereof have been attracting attention. In order to obtain these mesenchymal stem cells in large amounts while maintaining the performance of the stem cells, a method of culturing these cells is important.

For the culture and maintenance of adipose-derived stem cells (ADSCs), a medium containing animal serum, particularly fetal bovine serum (FBS) is used in most cases. FBS contains various types of growth factors, proteins, vitamins and hormones (Wassman S. J et al., *Dev Biol Stand* 99:3-8, 1999), and thus is relatively suitable for use in stem cell culture, but the risk factors of animal-derived raw materials for use in cell culture cannot be completely eliminated.

In order to eliminate these risk factors, various serum-free media containing no FBS have recently been developed and marketed, and suitable serum-free media may be selected and used depending on the type of cell. However, the efficiency of culture performed using serum-free media is very low in most cases compared to when culture is performed using serum-containing media (Mannello F. et al., *Stem Cells*. 25(7):1603-9, 2007). In order to overcome this problem, additional treatment with various additives is required. Thus, the proliferation rate of cells in serum-free media is relatively low, and various growth factors and additives that are added to serum-free media impose considerable cost burdens.

As one of methods capable of solving the problems with cost burden and reduced cell proliferation in the production process, gamma-irradiated sterile FBS may be used. Gamma ray, electron beam and X-ray irradiation technologies are cold sterilization and insecticidal technologies that eliminate harmful components in completely packaged products without a rise in temperature. This effect is achieved by damaging cellular components, such as DNA, proteins, or lipids, through the direct and indirect action of radiation. Gamma irradiation can further reduce or eliminate the spectrum of viruses and mycoplasmas that may be present even after sterile filtration. Thus, gamma-irradiation sterilization is recommended for animal-derived raw materials which are used in pharmaceutical processes worldwide.

However, proteins exposed to gamma rays change reversibly or irreversibly (Cho Yong Sik, Chungnam National University Dissertation, 1999), and free radicals generated after gamma irradiation damage various growth factors. In other words, there is a possibility that the growth factors in FBS can be destroyed by gamma irradiation.

Accordingly, the present inventors have made extensive efforts to produce stem cells which are free from risk factors, such as infection, and thus are safe for use as cell therapy agents. As a result, the present inventors have found that when stem cells are cultured in a medium containing gamma-irradiated serum and an antioxidant, stem cells which have improved adhesion and proliferation rate and are excellent for use as cell therapy agents can be produced, thereby completing the present invention.

DISCLOSURE OF INVENTION

It is an object of the present invention to provide a method of culturing mesenchymal stem cells, which can improve the adhesion and proliferation rate of stem cells using a medium containing gamma-irradiated serum and an antioxidant.

To achieve the above object, the present invention provides a method for culturing mesenchymal stem cells, comprising the steps of: (a) irradiating fetal bovine serum (FBS) with gamma radiation; (b) adding the gamma-irradiated fetal bovine serum to a stem cell culture medium; and (c) culturing mesenchymal stem cells using the culture medium.

ADVANTAGEOUS EFFECTS

The method for culturing mesenchymal stem cells according to the present invention can restore the adhesion and proliferation rate of stem cells when culturing the stem cells using gamma-irradiated FBS, which is safe from contamination sources but reduces the efficiency of adhesion and proliferation of the cells. Thus, the inventive method is useful for the production of stem cells for cell therapy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows stem cells cultured in a medium containing FBS sterilized by gamma irradiation and vitamin C (a vitamin C post-treatment group).

FIG. 2 shows the results of examining cell number and cell doubling time after 4 days of culture in a medium containing FBS sterilized by gamma irradiation and vitamin C (a vitamin C post-treatment group).

FIG. 3 shows a comparison between stem cells cultured in a medium containing FBS sterilized by gamma irradiation after pre-treatment with vitamin C (a vitamin C pre-treatment group) and stem cells cultured in a medium containing FBS sterilized by gamma irradiation and vitamin C (a vitamin C post-treatment group).

FIG. 4 shows the results of examining cell number and cell doubling time after 4 days of culture in a medium (a vitamin C pre-treatment group) containing FBS sterilized by gamma irradiation after pre-treatment with vitamin C or in a medium (a vitamin C post-treatment group) supplemented with FBS sterilized by gamma irradiation and vitamin C.

FIG. 5 shows the time before subculture of stem cells cultured in a medium containing FBS sterilized by gamma irradiation after pre-treatment with vitamin C (a vitamin C pre-treatment group) and stem cells cultured in a medium containing FBS sterilized by gamma irradiation and vitamin C (a vitamin C post-treatment group).

FIG. 6 shows a comparison between stem cells cultured in a medium containing FBS sterilized by 30 kGy gamma irradiation after pre-treatment with vitamin C (a vitamin C pre-treatment group), stem cells cultured in a medium containing FBS sterilized by 30 kGy gamma irradiation and vitamin C (a vitamin C post-treatment group), and stem cells cultured for 4 days in a medium containing FBS sterilized by 30 kGy gamma irradiation after pre-treatment with vitamin C and also containing vitamin C (vitamin C pre-treatment and post-treatment groups).

FIG. 7 shows a comparison of cell number between stem cells cultured in a medium containing FBS sterilized by 30 kGy gamma irradiation after pre-treatment with vitamin C (a vitamin C pre-treatment group), stem cells cultured in a medium containing FBS sterilized by 30 kGy gamma irradiation and vitamin C (a vitamin C post-treatment group), and stem cells cultured for 4 days in a medium containing FBS sterilized by 30 kGy gamma irradiation after pre-treatment with vitamin C and also containing vitamin C (vitamin C pre-treatment and post-treatment groups).

FIG. 8 shows a comparison of cell size between stem cells cultured in a medium containing FBS sterilized by 30 kGy gamma irradiation after pre-treatment with vitamin C (a vitamin C pre-treatment group), stem cells cultured in a medium containing FBS sterilized by 30 kGy gamma irradiation and vitamin C (a vitamin C post-treatment group), and stem cells cultured for 4 days in a medium containing FBS sterilized by 30 kGy gamma irradiation after pre-treatment with vitamin C and also containing vitamin C (vitamin C pre-treatment and post-treatment groups).

FIG. 9 shows a comparison of cell viability between stem cells cultured in a medium containing FBS sterilized by 30 kGy gamma irradiation after pre-treatment with vitamin C (a vitamin C pre-treatment group), stem cells cultured in a medium containing FBS sterilized by 30 kGy gamma irradiation and vitamin C (a vitamin C post-treatment group), and stem cells cultured for 4 days in a medium containing FBS sterilized by 30 kGy gamma irradiation after pre-treatment with vitamin C and also containing vitamin C (vitamin C pre-treatment and post-treatment groups).

FIG. 10 shows a comparison of cell doubling time between stem cells cultured in a medium containing FBS sterilized by 30 kGy gamma irradiation after pre-treatment with vitamin C (a vitamin C pre-treatment group), stem cells cultured in a medium containing FBS sterilized by 30 kGy gamma irradiation and vitamin C (a vitamin C post-treatment group), and stem cells cultured for 4 days in a medium containing FBS sterilized by 30 kGy gamma irradiation after pre-treatment with vitamin C and also containing vitamin C (vitamin C pre-treatment and post-treatment groups).

FIGS. 11A-11C show the results of examining the cell adhesion of stem cells cultured in a medium containing FBS sterilized by 30 kGy gamma irradiation and vitamin C (a vitamin C post-treatment group). Specifically, FIGS. 11A, 11B and 11C show cells at passage 1, passage 2 and passage 3, respectively.

FIG. 12 shows the results of FACS performed to analyze the expression of stem cell CD markers in the stem cells cultured in a medium containing FBS sterilized by 30 kGy gamma irradiation and vitamin C (a vitamin C post-treatment group).

FIG. 13 shows the induction of differentiation of stem cells cultured in a medium containing FBS sterilized by 30 kGy gamma irradiation and vitamin C (a vitamin C post-treatment group) into adipocytes.

FIG. 14 shows the induction of differentiation of stem cells cultured in a medium containing FBS sterilized by 30 kGy gamma irradiation and vitamin C (a vitamin C post-treatment group) into osteocytes.

FIG. 15 shows the induction of differentiation of stem cells cultured in a medium containing FBS sterilized by 30 kGy gamma irradiation and vitamin C (a vitamin C post-treatment group) into chondrocytes.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In the present invention, efforts were made to produce stem cells for cell therapy using gamma-irradiated FBS (fetal bovine serum) which can be completely free from the risk factors of animal-derived FBS that cannot be solved by heat inactivation or filtration, and as a result, free radicals generated by gamma irradiation could be solved using an antioxidant. In other words, the adverse effects of gamma irradiation of FBS on the adhesion and proliferation of stem cells could be eliminated using an antioxidant.

Therefore, in one aspect, the present invention is directed to a method for culturing mesenchymal stem cells, comprising the steps of: (a) irradiating fetal bovine serum (FBS) with gamma radiation; (b) adding the gamma-irradiated fetal bovine serum to a stem cell culture medium; and (c) culturing mesenchymal stem cells using the culture medium.

In the present invention, the fetal bovine serum used in step (a) may contain or not contain an antioxidant, and the antioxidant is preferably added in an amount of 0.025% to 2%, and is most preferably added in an amount of 1%, but is not limited thereto.

Serum proteins act as a carrier that delivers nutrients, such as lipids and enzymes, into cells (Stein A et al., *Biotechniques* 43:228-229, 2007; Sterodimas A et al., *J Plast Reconstr Aesthet Surg* 63:1886-1892, 2010). Generally, cell culture media contain vitamins, inorganic salts, hormones, and growth factors, and are supplemented with FBS for supply of nutrients that are required in trace amounts depending on the type of cells.

Gamma-irradiated fetal bovine serum is suitable for the most stringent aseptic requirements set for applications, such as virus and vaccine production, biopharmaceutical production processes and diagnostic products production.

In the present invention, the stem cell culture medium in step (b) may contain an antioxidant, and the antioxidant is preferably added in an amount of 0.025% to 2%, and is most preferably added in an amount of 1%, but is not limited thereto.

As additives for increasing the efficiency of culture, vitamins, inorganic salts, hormones, etc. are added to basal medium in more diverse kinds or at high concentrations to enhance the nutrients of the basal medium, and particular growth factors are also added depending on the type of cells (Maurer H R et al., *Send to Cytotechnology.* 5(1):1, 1991).

In the present invention, the antioxidant may be selected from the group consisting of vitamin C (ascorbic acid), selenium, coenzyme Q10, vitamin E, catechin, lycopene, beta carotene, EPA (eicosapentaenoic acid), and DHA (docosahexanoic acid).

Krumahar et al. have reported the effect of ascorbic acid on the solubility of gamma-irradiated lactalbumin (Krumhar et al., *J. Food Sci.* 55:1127-1132, 1990). The effect of oxygen on protein damage caused by radiation irradiation is well known (Singh, A et al., *Methods in Enzymology,* 186:686-696, 1990), and oxygen promotes the biological damage caused by radiation irradiation, and thus antioxidants can be substances that inhibit radiation damage (Bienvenu, P et al., *Adv. Exp. Med. Biol.* 264:291-300, 1990). In fact, most of substances that inhibit biological damage caused by radiation are antioxidants (Bienvenu, P et al., *Adv. Exp. Med. Biol.* 264:291-300, 1990). Ascorbic acid, an essential vitamin, acts as antioxidant and has been widely used together with tocopherol in studies on inhibition of radiation damage, which are performed through animal experiments (El-Nahas S. M et al., *Mutat. Res.* 301:143-147, 1993; O 'Connor M. K et al., *Br. J. Radiol.* 50:587-591, 1977; Niki, E et al., *Ann. N. Y. Acad. Sci.* 498:186-199, 1987; Niki, E et al., *J. Biol. Chem.* 259:4177-4182, 1984; Rana, K et al., *Indian J. Exp. Biol.* 31:847-849, 1993). It is known that ascorbic acid reacts with free radicals, is readily oxidized by radiation irradiation (Woods, R. J et al., Applied radiation chemistry pp 443-447, 1994), and has strong reactivity when oxidized to dehydroascorbic acid (Kacem, B et al., *J. Food Sci.* 52:1665-1672, 1987). The effective inhibition of radiation damage by ascorbic acid against radical formation is understood in terms of the fact that ascorbic acid eliminates protein radicals (Cho Yong Sik, Chungnam National University Dissertation, 1999).

The term "AA2P pre-treatment" or "vitamin C pre-treatment" of the present invention means treating antioxidant with FBS followed by gamma irradiation. That is, gamma-irradiated FBS containing antioxidants is added to culture medium.

The term "AA2P post-treatment" or "vitamin C post-treatment" of the present invention means that FBS without antioxidant is gamma-irradiated and then added together with antioxidants when it is treated in the culture medium.

In one example of the present invention, the stem cells cultured in a medium containing FBS sterilized by gamma irradiation had remarkably reduced adhesion and proliferation rate.

In one example of the present invention, a study was conducted with 25 kGy which is a minimum radiation dose specified in the US FDA guidelines.

In the present invention, the gamma irradiation is performed with an absorbed dose of preferably 20 to 35 kGy, but is not limited thereto.

As studies on irradiated proteins, many studies have been conducted on proteins or amino acids constituting proteins (Garrison, W. M et al. *Chem Rev.* 87:381-398, 1987). These studies show that the molecular weights of proteins are increased or decreased by chain reactions of either primary radical ions generated by irradiation or secondary radical ions generated from water molecules bound to the proteins (Davies, K. J. A et al., *J. Biol. Chem.* 262:9895-9901, 1987). In addition, study results were also reported which indicate that when a protein is irradiated with radiation, the molecular structure thereof is changed and the enzymatic activity and immunological properties thereof are changed (Yook, H. S et al. *J. Kor. Soc. Food Sci. Nutr.* 26:1116-1121, 1997). That is, free radicals generated after gamma irradiation can damage various growth factors.

The above-described results are a problem to be solved in stem cell culture which is performed using gamma-irradiated FBS safe from contamination sources.

In the present invention, the fetal bovine serum in step (b) may be added in an amount of 2% to 10%, and is preferably added in an amount of 5%, but is not limited thereto.

In culture of stem cells for use as a cell therapy agent, serum-free culture or gamma-irradiated FBS can be used as a method capable of eliminating risk factors such as infection, which cannot be solved by heat inactivation or filtration.

However, the serum-free culture shows a relatively low proliferation rate. Thus, in order to increase the efficiency thereof, additives, such as vitamins, inorganic salts and hormones, are added to basal medium at high concentrations to enhance the nutrients of the basal medium, and particular growth factors are also added depending on the type of cells (Maurer H R et al., *Send to Cytotechnology.* 5(1):1, 1991).

Gamma-irradiated FBS can further reduce or eliminate the spectrum of viruses and mycoplasmas that may be present even after sterile filtration. The radiation sensitivity of microorganisms varies depending on temperature, oxygen conditions, and water activity. Specifically, the effect of radiation on organisms increases with increasing temperature, oxygen content and water activity, and thus microorganisms can be controlled with a relatively low radiation dose.

At present, radiation sterilization technology is used for long-term storage of food resources, which requires inhibition of seed germination/rooting of agricultural products, retardation of maturity, control of pests and parasites, and disinfection of spoilage microorganisms, and is also used for the development of space food, relief food and patient food. In addition, radiation sterilization technology is used as the most effective technology capable of replacing chemical preservatives and fumigants in the sterilization treatment of public health products including medicines, and in the quarantine and disinfection treatment of agricultural products between countries. In the field of regenerative medicine, radiation treatment is recommended as an international standard technology to remove pathogenic microorganisms from allogeneic and xenogeneic tissues. It is expected that a lot of research and development will be carried out in the future to reduce the immune rejection of xenogeneic biomaterials and ensure the safety of these materials (Kim Jae-Kyung et al., Journal of the Korean Musculoskeletal Tissue Transplantation Society, 13(2):49-57, 2013).

In the present invention, the stem cell culture medium in step (b) may be a 1:1 mixture of KSFM-P medium (containing Defined Keratinocyte-SFM, 0.05 to 1 mM L-ascorbic acid 2-phosphate, 0.1 to 100 µg/ml insulin, 0.2 to 20 mM N-acetyl-L-cysteine, 0.01 to 1 mM calcium chloride, 5 ng/ml to 1 µg/ml hydrocortisone and 5% FBS) and DMEM medium. More preferably, the contents of L-ascorbic acid 2-phosphate, insulin, N-acetyl-L-cysteine, calcium chloride, hydrocortisone and FBS are 0.2 mM, 5 µg/ml, 2 mM, 0.09 mM, 74 ng/ml and 5%, respectively, but are not limited thereto.

In the present invention, the mesenchymal stem cells are preferably derived from adipose tissue, but are not limited thereto.

In the present invention, medium containing FBS irradiated with 25 to 30 kGy of gamma radiation was treated with 1% vitamin C, and then stem cells were adhered to and cultured in the medium. As a result, it could be confirmed that the proliferation rate and adhesion of the stem cells were similar to those of a positive control group cultured using normal FBS which was not irradiated with gamma radiation.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Isolation of Human Adipose Tissue-Derived Mesenchymal Stem Cells

Human adipose tissue obtained from abdominal adipose by liposuction was isolated and washed with PBS. The tissue was cut finely, and then degraded using DMEM medium containing collagenase type 1 (1 mg/ml) at 37° C. for 2 hours. The collagenase-treated tissue was washed with PBS, and then centrifuged at 1000 rpm for 5 minutes. The supernatant was removed, and the pellet was washed with PBS, and then centrifuged at 1000 rpm for 5 minutes. The floating material was removed by filtration through a 100 µm mesh, and then the remaining material was washed with PBS and cultured in DMEM medium containing 10% FBS, 2 mM NAC (N-acetyl-L-cysteine) and 0.2 mM ascorbic acid. After one-night standing, non-adherent cells were washed out with PBS, and the adherent cells were subcultured in Keratinocyte-SFM medium containing 5% FBS, 2 mM NAC, 02 mM ascorbic acid, 0.09 mM calcium, 5 ng/ml rEGF, 5 µg/ml insulin, 10 ng/ml bFGF and 74 ng/ml hydrocortisone while replacing the medium at 2-day intervals, thereby isolating adipose tissue-derived mesenchymal stem cells.

Example 2: Culture of Stem Cells Using Gamma-Irradiated FBS

Fetal bovine serum (FBS) was irradiated with 25 kGy of gamma radiation (Soyagreentec Co., Ltd.), thereby preparing gamma-irradiated FBS.

Then, the human adipose tissue-derived stem cells at passage 3, isolated in Example 1, were thawed and inoculated into T75 flasks at a concentration of $0.5 \times 10^6$ cells/T75 flask, and the inoculated cells were cultured with AMSC+ culture medium (R-Bio Co., Ltd.) containing the prepared gamma-irradiated FBS at a concentration of 5% in a CO2 incubator at 37° C. for 2 days. After 2 days of culture, the medium was removed and replaced with either AMSC+ culture medium containing 5% gamma-irradiated FBS (a negative control group) or medium obtained by adding vitamin C (ascorbic acid; L-Ascorbic Acid 2-phosphate) to AMSC+ culture medium containing 5% gamma-irradiated FBS (a vitamin C post-treatment test group). Vitamin C was added to the culture medium at concentrations of 0.025, 0.05, 0.1 and 1%. The AMSC+ culture medium (R-Bio Co., Ltd.) is a 1:1 mixture of KSFM-P medium (containing Defined Keratinocyte-SFM, 0.2 mM L-ascorbic acid 2-phosphate, 5 µg/ml insulin, 2 mM N-acetyl-L-cysteine, 0.09 mM calcium chloride, 74 ng/ml hydrocortisone and 5% FBS) and DMEM medium.

After 4 days of culture, the cell proliferation rate and doubling time of the cells were examined. The viability of the cells was examined with a microscope and a hemocytometer, and the doubling time was calculated using the following equation:

$$\text{Doubling Time} = \text{duration} \times \log(2)/\log(\text{final concentration}) - \log(\text{initial concentration}). \qquad \text{[Equation 1]}$$

A positive control group was cultured using 5% normal FBS (which was not irradiated with gamma radiation) and AMSC+ culture medium in the same manner as the negative control group and the test group.

As a result, as shown in Table 1 below and FIG. 2, the stem cells cultured in the medium containing gamma-irradiated FBS (the negative control group) showed a decrease in cell number and an increase in doubling time. However, in stem cells cultured for 4 days in culture medium containing gamma irradiated gamma-sterilized FBS and supplemented with vitamin C (ascorbic acid; L-Ascorbic Acid 2-phosphate) (vitamin C post-treatment experimental group), the cell number of cells increased compared to the negative control group, and the doubling time decreased compared to the negative control group.

TABLE 1

| Ad-MSC (P4) | Cell No. (×10^6 cells) | Doubling time (hr) |
| --- | --- | --- |
| Positive cont. | 18 | 24.57 |
| Negative cont. (25 KGy) | 8.85 | 33.3 |
| 25 KGy + 0.025% AA2P | 10.035 | 31.33 |
| 25 KGy + 0.05% AA2P | 9.5 | 32.16 |
| 25 KGy + 0.1% AA2P | 10.6 | 30.54 |
| 25 KGy + 1% AA2P | 12 | 28.9 |

In addition, the stem cells in each of the media were observed with a microscope on days 0, 1 and 4, and as a result, the stem cells cultured in the medium obtained by adding vitamin C (ascorbic acid; L-ascorbic acid 2-phosphate) to the AMSC+ culture medium containing gamma-irradiated FBS (the vitamin C post-treatment test group) showed levels similar to those of the positive control group (FIG. 1).

Example 3: Culture of Stem Cells Using Gamma-Irradiated FBS Containing Antioxidant Fetal bovine serum (FBS) was irradiated with 25 kGy of gamma radiation, thereby preparing gamma-irradiated FBS.

Vitamin C (ascorbic acid; L-Ascorbic Acid 2-phosphate) was added to the FBS which was then irradiated with 25 kGy of gamma irradiation, thereby preparing gamma-irradiated FBS pretreated with vitamin C. The vitamin C was added to the FBS at a concentration of 0.1% or 1%.

Then, the human adipose tissue-derived stem cells at passage 3, isolated in Example 1, were thawed and inoculated into T75 flasks at a concentration of $0.5 \times 10^6$ cells/T75 flask, and the inoculated cells were cultured with AMSC+ culture medium (R-Bio Co., Ltd.) containing the prepared gamma-irradiated FBS or gamma-irradiated FBS pretreated with vitamin C at a concentration of 5% in a CO2 incubator at 37° C. for 2 days. After 2 days of culture, the medium was removed and replaced with AMSC+ culture medium containing 5% gamma-irradiated FBS (a negative control group), medium obtained by adding vitamin C to AMSC+ culture medium containing 5% gamma-irradiated FBS (a vitamin C post-treatment test group), or AMSC+ culture medium containing 5% gamma-irradiated FBS pretreated with vitamin C (a vitamin C pre-treatment test group). Vitamin C was added to the culture medium or FBS at a concentration of 0.1 or 1%. After 4 days of culture, the cell proliferation rate and doubling time of the cells were examined in the same manner as described in Example 2 above. A positive control group was also prepared as described in Example 2 above.

As a result, as shown in Table 2 below and FIG. 4, the stem cells cultured in the medium containing gamma-irradiated FBS (the negative control group) showed a decrease in cell number and an increase in doubling time, but the cell number and doubling time of the stem cells cultured for 4 days in the medium obtained by adding vitamin C to the AMSC+ culture medium containing gamma-irradiated FBS (a vitamin C post-treatment test group) and AMSC+ culture medium containing gamma-irradiated FBS pretreated with vitamin C (a vitamin C pre-treatment test group) were increased to the levels of the positive control group.

TABLE 2

| Ad-MSC (P4) | Cell No. ($\times 10^{\wedge}6$ cells) | Doubling time (hr) |
| --- | --- | --- |
| Positive cont. | 10.7 | 21 |
| Negative cont. (25 KGy) | 8.0 | 23 |
| 0.1% AA2P pre-treatment + 25 KGy | 10.2 | 21 |
| 1% AA2P pre-treatment + 25 KGy | 10.0 | 21 |
| 0.1% AA2P post-treatment + 25 KGy | 10.6 | 21 |
| 1% AA2P post-treatment + 25 KGy | 14.0 | 19 |

In addition, the stem cells in each of the media were observed with a microscope on day 4, and as a result, the stem cells cultured in the medium obtained by adding vitamin C to the AMSC+ culture medium containing gamma-irradiated FBS (the vitamin C post-treatment test group) and AMSC+ culture medium containing gamma-irradiated FBS pretreated with vitamin C (a vitamin C pre-treatment test group) showed levels similar to those of the positive control group (FIG. 3).

Example 4: Adhesion of Stem Cells Cultured in FBS Irradiated with 25 kGy of Gamma Radiation In the same manner as described in Example 3 above, fetal bovine serum (FBS) was irradiated with 25 kGy of gamma radiation, thereby preparing gamma-irradiated FBS. Vitamin C (ascorbic acid; L-Ascorbic Acid 2-phosphate) was added to the FBS which was then irradiated with 25 kGy of gamma irradiation, thereby preparing gamma-irradiated FBS pretreated with vitamin C. The vitamin C was added to the FBS at a concentration of 1%.

Then, the human adipose tissue-derived stem cells at passage 0, isolated in Example 1, were thawed and inoculated into T25 flasks at a concentration of $1.7 \times 10^3$ cells/T25 flask, and the inoculated cells were cultured with AMSC+ culture medium (R-Bio Co., Ltd.) containing the prepared gamma-irradiated FBS or gamma-irradiated FBS pretreated with vitamin C at a concentration of 5% in a CO2 incubator at 37° C. for 2 days. After 2 days of culture, the medium was removed and replaced with AMSC+ culture medium containing 5% gamma-irradiated FBS (a negative control group), medium obtained by adding vitamin C to AMSC+ culture medium containing 5% gamma-irradiated FBS (a vitamin C post-treatment test group), or AMSC+ culture medium containing 5% gamma-irradiated FBS pretreated with vitamin C (a vitamin C pre-treatment test group). Vitamin C was added to the culture medium or FBS at a concentration of 1%. A positive control group was also prepared as described in Examples 2 and 3 above.

For each control group and the test group, examination was performed of the time at which the density of the stem cells reached 90% so that these cells could be sub-cultured.

As a result, as shown in Table 3 below and FIG. 5, in the positive control group in 5% normal FBS (not irradiated with gamma radiation) and AMSC+ culture medium, the stem cell density reached 90% on day 10 of culture, and in the stem cells cultured in the medium containing gamma-irradiated FBS (the negative control group), there were little or no adherent cells on both day 8 and day 13 of culture. However, the stem cells cultured in the medium obtained by adding vitamin C to the AMSC+ culture medium containing gamma-irradiated FBS (the vitamin C post-treatment test group), and the stem cells cultured in the AMSC+ culture medium containing the gamma-irradiated FBS pretreated with vitamin C (the vitamin C pre-treatment test group) showed a stem cell density of 90% on day 13 and day 10, similar to the positive control group.

TABLE 3

| Group | Density (90%) |
| --- | --- |
| Positive control | Day 10 |
| Negative control | — |
| Pre-treatment with Vit. C | Day 13 |
| Post-treatment with Vit. C | Day 10 |

Example 5: Viability of Stem Cells Cultured in FBS Irradiated with 30 kGy of Gamma Radiation Fetal bovine serum (FBS) was irradiated with 30 kGy of gamma radiation, thereby preparing gamma-irradiated FBS. Vitamin C (ascorbic acid; L-Ascorbic Acid 2-phosphate) was added to the FBS which was then irradiated with 30 kGy of gamma irradiation, thereby preparing gamma-irradiated FBS pretreated with vitamin C. The vitamin C was added to the FBS at a concentration of 1%.

Then, the human adipose tissue-derived stem cells at passage 3, isolated in Example 1, were thawed and inoculated into T75 flasks at a concentration of $0.5 \times 10^6$ cells/T75 flask, and the inoculated cells were cultured with AMSC+ culture medium (R-Bio Co., Ltd.) containing the prepared gamma-irradiated FBS or gamma-irradiated FBS pretreated with vitamin C at a concentration of 5% in a CO2 incubator at 37° C. for 2 days. After 2 days of culture, the medium was removed and replaced with AMSC+ culture medium containing 5% gamma-irradiated FBS (a negative control group), medium obtained by adding vitamin C to AMSC+ culture medium containing 5% gamma-irradiated FBS (a vitamin C post-treatment test group), or medium obtained by adding vitamin C to AMSC+ culture medium containing 5% gamma-irradiated FBS pretreated with vitamin C (a vitamin C pre- and post-treatment test group) (Table 4). Vitamin C was added to the culture medium or FBS at a concentration of 1%. After 4 days of culture (FIG. 6), the cell proliferation rate, cell number, viability and doubling time of the stem cells were examined. A positive control group was also prepared as described in Example 2 above.

TABLE 4

| | |
|---|---|
| Positive control group | Cultured in AMSC+ medium containing FBS (normal) |
| Negative control group | AMSC+ medium containing FBS irradiated with 30 kGy of gamma radiation |
| 1% vitamin C pre-treatment Group | AMSC+ medium containing 30 kGy gamma-irradiated FBS treated with vitamin C |
| 1% vitamin C post-treatment group | Vitamin C post-treatment of AMSC+ medium containing 30 kGy gamma-irradiated FBS |
| 1% vitamin C pre + post-treatment group | Vitamin C post-treatment of AMSC+ medium containing 30 kGy gamma-irradiated FBS treated with vitamin C |

As a result, as shown in Table 5 below and FIGS. 7 to 10, the stem cells cultured in the medium containing gamma-irradiated FBS (the negative control group) showed a decrease in cell number and cell viability and an increase in doubling time, but the cell number, viability and doubling time of the stem cells cultured for 4 days in the medium obtained by adding vitamin C to the AMSC+ culture medium containing gamma-irradiated FBS (a vitamin C post-treatment test group) were increased to the levels of the positive control group.

TABLE 5

| | Average (n = 3) | | | |
|---|---|---|---|---|
| Group | Cell No. ($\times 10^6$ cells) | Cell size (µm) | Viability (%) | DT(hr) |
| Positive Control | 6.2 | 19.3 | 88.5 | 27.1 |
| Negative Control | 3.8 | 19.5 | 86.7 | 32.3 |
| 1% Vit. C post-treatment | 4.3 | 19.3 | 86.9 | 29.9 |
| 1% Vit. C pre-treatment | 5.8 | 18.8 | 92.3 | 27.6 |
| 1% Vit. C pre-treatment + 1% Vit. C post-treatment | 5.7 | 20.3 | 86.5 | 28.1 |

Example 6: Adhesion and Proliferation Rate of Stem Cells Cultured in 30 kGy Gamma-Irradiated FBS Fetal bovine serum (FBS) was irradiated with 30 kGy of gamma radiation, thereby preparing gamma-irradiated FBS. The gamma-irradiated FBS was added to AMSC+ culture medium (R-Bio Co., Ltd.) at a concentration of 5%, and 1% vitamin C was added to the culture medium, thereby preparing a medium (a vitamin C post-treatment group).

Then, the human adipose tissue-derived stem cells at passage 1, isolated in Example 1, were thawed and inoculated into T25 flasks at a concentration of $0.7 \times 10^3$ cells/T25 flask, and the inoculated cells were cultured with AMSC+ culture medium (R-Bio Co., Ltd.) containing the prepared gamma-irradiated FBS at a concentration of 5% in a CO2 incubator at 37° C. for 2 days. After 2 days of culture, the medium was removed and replaced with AMSC+ culture medium containing 5% normal FBS (a positive control group), or medium obtained by adding vitamin C to AMSC+ culture medium containing 5% gamma-irradiated FBS (a vitamin C post-treatment test group). Vitamin C was added to the culture medium at a concentration of 1%.

For the positive control group and the vitamin C post-treatment group, the stem cells at passages 2 to 4 were examined for their adhesion (FIGS. 11A to 11C), their cell number, cell size and viability (Tables 6 to 9). The stem cell adhesion shown in FIGS. 11A-11C was examined with a Leica microscope, and the cell number, cell size and viability shown in Tables 6 to 9 were examined with Luna™ Automated cell counter L10001 (Logos Biosystems).

As a result, the adhesion, cell number, cell size and viability of the stem cells at passages 2 to 4 did not differ from those of the positive control group.

TABLE 6

| Stem cells | | Cell number ($\times 10^7$ cells) | Cell size (µm) | Viability (%) |
|---|---|---|---|---|
| #1 P1 | P.C | $2.7 \times 10^7$ cells | 20 µm | 83.2% |
| | Vitamin C post-treatment | $2.4 \times 10^7$ cells | 19.1 µm | 84.4% |
| #2 P1 | P.C | $1.9 \times 10^7$ cells | 20 µm | 80.2% |
| | Vitamin C post-treatment | $1.8 \times 10^7$ cells | 20 µm | 89.6% |
| #3 P1 | P.C | $2.8 \times 10^7$ cells | 20 µm | 85% |
| | Vitamin C post-treatment | $2.3 \times 10^7$ cells | 19.6 µm | 87.1% |

TABLE 7

| Stem cells | | Cell number ($\times 10^7$ cells) | Cell size (µm) | Viability (%) |
|---|---|---|---|---|
| #1 P2 | P.C | $1.6 \times 10^7$ cells | 19.8 µm | 88.3% |
| | Vitamin C post-treatment | $1.6 \times 10^7$ cells | 19.5 µm | 83% |
| #2 P2 | P.C | $1.5 \times 10^7$ cells | 20 µm | 82.8% |
| | Vitamin C post-treatment | $1.8 \times 10^7$ cells | 19.3 µm | 95.5% |
| #3 P2 | P.C | $1.3 \times 10^7$ cells | 19 µm | 84.2% |
| | Vitamin C post-treatment | $1.4 \times 10^7$ cells | 18 µm | 82% |

TABLE 8

| Stem cells | | Cell number ($\times 10^7$ cells) | Cell size (µm) | Viability (%) |
|---|---|---|---|---|
| #1 P3 | P.C | $1.6 \times 10^7$ cells | 19 µm | 90.8% |
| | Vitamin C post-treatment | $2.0 \times 10^7$ cells | 19.2 µm | 88.7% |
| #2 P3 | P.C | $1.3 \times 10^7$ cells | 20 µm | 98.3% |
| | Vitamin C post-treatment | $1.2 \times 10^7$ cells | 19.7 µm | 88.9% |
| #3 P3 | P.C | $1.3 \times 10^7$ cells | 20 µm | 96.6% |
| | Vitamin C post-treatment | $1.4 \times 10^7$ cells | 19.3 µm | 88.2% |

TABLE 9

| Stem cells | | Cell number (×10⁸ cells) | Cell size (μm) | Viability (%) |
|---|---|---|---|---|
| #1 P4 | P.C | 2.8 × 10⁸ cells | 19.8 μm | 97.6% |
| | Vitamin C post-treatment | 3.3 × 10⁸ cells | 20 μm | 87.5% |
| #2 P4 | P.C | 2.4 × 10⁸ cells | 18.8 μm | 83.0% |
| | Vitamin C post-treatment | 1.5 × 10⁸ cells | 18.8 μm | 95.6% |
| #3 P4 | P.C | 2.4 × 10⁸ cells | 18.5 μm | 84.0% |
| | Vitamin C post-treatment | 2.1 × 10⁸ cells | 17.8 μm | 88.0% |

Example 7: Characteristics of Stem Cells Cultured in Medium Containing Gamma-Irradiated FBS and Post-Treated with Vitamin C For the positive control group and vitamin C post-treatment test group of Example 6, the purity and characteristics of the stem cells at passage 4 were examined.

The purity of the stem cells was examined by analyzing the expression of CD markers using FACS (FIG. 12 and Table 10), and the characteristics of the stem cells were examined by analyzing differentiation into adipocytes, osteocytes and chondrocytes (FIGS. 13 to 15). Differentiation into adipocytes was analyzed by oil red 0 staining according to the Sigma-Aldrich protocol, and differentiation into osteocytes was analyzed by alizarin red S staining according to the Lifeline Cell Tech's protocol, and differentiation into chondrocytes was analyzed by TSP2 ELISA.

TABLE 10

| Stem cells | | CD73 | CD90 | CD31 | CD34 | CD45 | CD73 |
|---|---|---|---|---|---|---|---|
| #1 P4 | P.C | 82.47 | 100 | 0.27 | 0.31 | 0.17 | 82.47 |
| | Vitamin C post-treatment | 94.30 | 99.98 | 0.52 | 0.31 | 0.49 | 94.30 |
| #2 P4 | P.C | 95.73 | 99.97 | 0.24 | 0.10 | 0.09 | 95.73 |
| | Vitamin C post-treatment | 93.42 | 99.99 | 0.16 | 0.14 | 0.11 | 93.42 |
| #3 P4 | P.C | 92.75 | 99.99 | 0.02 | 0.00 | 0.02 | 92.75 |
| | Vitamin C post-treatment | 91.45 | 99.99 | 0.47 | 0.70 | 0.78 | 91.45 |

As a result, the expression of CD markers in the test group irradiated with 30 KGy of gamma radiation and post-treated with 1% vitamin C did not differ from that in the positive control group, and the characteristics of differentiation of the test group into adipocytes, osteocytes and chondrocytes also did not differ from those of the positive control group.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for culturing mesenchymal stem cells in a culture medium, comprising the steps of (a)-(c) or (a')-(c'):
    (a) preparing vitamin C pre-treated gamma-sterilized fetal bovine serum (FBS) by irradiating gamma rays to FBS pre-treated with 0.1-1% of vitamin C;
    (b) culturing mesenchymal stem cells for 2 days in a stem cell culture medium containing the vitamin C pre-treated gamma-sterilized FBS; and
    (c) further culturing in a stem cell culture medium containing gamma-irradiated FBS and 0.1-1% of vitamin C or a stem cell culture medium containing the vitamin C pre-treated gamma-sterilized FBS; or
    (a') preparing vitamin C post-treated gamma-sterilized FBS by treating 0.1-1% of vitamin C to gamma-irradiated FBS;
    (b') culturing the mesenchymal stem cells for 2 days in a stem cell culture medium containing the vitamin C post-treated gamma-sterilized FBS; and
    (c') further culturing in a culture medium containing gamma-irradiated FBS and 0.1-1% vitamin C;
    wherein the stem cell culture medium is a mixture of KSFM-P(Keratinocyte Serum Free Medium-P) medium and DMEM(Dulbecco's Modified Eagle's Medium) medium; and
    wherein the cell number, viability, and doubling time of the cultured mesenchymal stem cells are at the same level as mesenchymal stem cells that have been cultured by medium supplemented with gamma-irradiated FBS for 2 days, and thereafter cultured by medium supplemented with non-irradiated FBS.

2. The method of claim 1, wherein a concentration of the gamma-irradiated FBS is 2% to 10%.

3. The method of claim 1, wherein the KSFM-P medium contains Defined Keratinocyte-SFM(Serum-Free Medium), L-ascorbic acid 2-phosphate, insulin, N-acetyl-L-cysteine, calcium chloride, hydrocortisone and FBS.

4. The method of claim 1, wherein the FBS is gamma-irradiated with an absorbed dose of 20 to 35 kGy.

5. The method of claim 1, wherein the mesenchymal stem cells are derived from adipose tissue.

* * * * *

UNITED STATES PATENT AND TRADEMARK OFFICE
CERTIFICATE OF CORRECTION

PATENT NO. : 11,932,874 B2
APPLICATION NO. : 16/422525
DATED : March 19, 2024
INVENTOR(S) : Ra et al.

Page 1 of 1

It is certified that error appears in the above-identified patent and that said Letters Patent is hereby corrected as shown below:

In the Specification

Column 10, Line 6, "$1.7 \times 10^3$ cells/T25" should be -- $1.7 \times 10^5$ cells/T25 --.

Column 11, Line 64, "$0.7 \times 10^3$ cells/T25" should be -- $0.7 \times 10^5$ cells/T25 --.

Column 13, Line 29, "oil red 0" should be -- oil red O --.

Signed and Sealed this
Thirtieth Day of April, 2024

Katherine Kelly Vidal
*Director of the United States Patent and Trademark Office*